US010459095B2

(12) United States Patent
Li et al.

(10) Patent No.: US 10,459,095 B2
(45) Date of Patent: Oct. 29, 2019

(54) FLAT-PLATE PET IMAGING DEVICE WITH WINDOW

(71) Applicant: RAYCAN TECHNOLOGY CO., LTD. (SU ZHOU), Suzhou (CN)

(72) Inventors: Bingxuan Li, Suzhou (CN); Peng Xiao, Suzhou (CN); Yanbin Guo, Suzhou (CN); Qingguo Xie, Suzhou (CN)

(73) Assignee: RAYCAN TECHNOLOGY CO., LTD. (SU ZHOU), Suzhou (CN)

( * ) Notice: Subject to any disclaimer, the term of this patent is extended or adjusted under 35 U.S.C. 154(b) by 0 days.

(21) Appl. No.: 16/067,579

(22) PCT Filed: Nov. 25, 2016

(86) PCT No.: PCT/CN2016/107263
§ 371 (c)(1),
(2) Date: Jun. 29, 2018

(87) PCT Pub. No.: WO2017/114046
PCT Pub. Date: Jul. 6, 2017

(65) Prior Publication Data
US 2019/0011580 A1 Jan. 10, 2019

(30) Foreign Application Priority Data
Dec. 30, 2015 (CN) .......................... 2015 1 1019068

(51) Int. Cl.
G01T 1/29 (2006.01)
A61B 6/12 (2006.01)
(Continued)

(52) U.S. Cl.
CPC ............ *G01T 1/2985* (2013.01); *A61B 6/037* (2013.01); *A61B 6/12* (2013.01); *A61B 6/4266* (2013.01)

(58) Field of Classification Search
CPC ..... G01T 1/2985; A61B 6/037; A61B 6/4266; A61B 6/12
(Continued)

(56) References Cited

U.S. PATENT DOCUMENTS

2011/0024637 A1 2/2011 Yamaya et al.
2016/0209515 A1* 7/2016 Da Silva Rodrigues ...................
G01T 1/1603

FOREIGN PATENT DOCUMENTS

CN 104856716 A 8/2015
CN 105105781 A 12/2015
(Continued)

OTHER PUBLICATIONS

Yamaya et al., "An Initial Investigation of Open PET Geometries," 2007 IEEE Nuclear Science Symposium Conference Record, manuscript received Nov. 23, 2007, pp. 3688-3690.
(Continued)

Primary Examiner — David P Porta
Assistant Examiner — Gisselle Gutierrez
(74) Attorney, Agent, or Firm — Arent Fox LLP

(57) ABSTRACT

Provided is a flat-plate PET imaging device with a window (11), comprising: a first flat plate (10) formed of a plurality of PET detectors arranged in sequence into a plate shape and provided with at least one window (11); a second flat plate (20) formed of a plurality of PET detectors arranged in sequence into a plate shape and parallel to the first flat plate (10) and the second flat plate (20) are fixed. By arranging a window (11) on the flat-plate PET, a space is provided for other operations, such as radiotherapy, while ensuing the real-time positioning and scanning effects, thereby actually achieving real-time diagnosis as well as positioning and navigation without affecting the therapeutic procedure.

20 Claims, 4 Drawing Sheets

(51) Int. Cl.
*A61B 6/03* (2006.01)
*A61B 6/00* (2006.01)

(58) Field of Classification Search
USPC .......................................................... 250/366
See application file for complete search history.

(56) References Cited

FOREIGN PATENT DOCUMENTS

| | | |
|---|---|---|
| CN | 205433730 U | 8/2016 |
| WO | 2015004661 A1 | 1/2015 |

OTHER PUBLICATIONS

International Search Report for PCT/CN2016/107263 dated Feb. 16, 2017.

\* cited by examiner

FLAT-PLATE PET IMAGING DEVICE WITH WINDOW

CROSS REFERENCE TO RELATED APPLICATIONS

This application is a United States National Stage Application under 35 U.S.C. § 371 of International Patent Application No. PCT/CN2016/107263, filed Nov. 25, 2016, entitled "FLAT PLATE PET IMAGING DEVICE WITH WINDOW," which claims the priority of CN application No. 201511019068.5, entitled "Flat Plate PET Imaging Device with Window" filed with the SIPO on Dec. 30, 2015, of which the entire contents have been incorporated herein and herewith by reference.

BACKGROUND

Technical Field

The present disclosure relates to a medical device, specifically to a flat-plate PET imagining device with a window.

INTRODUCTION

Of all diseases cancers pose one of the most serious threats to human life. Currently, cancers are generally treated with surgical operation, radiotherapy and chemotherapy. Radiotherapy, which uses rays generated by radioactive isotopes, regular X rays generated by an X-ray generator, high-energy X-rays generated by accelerators, electronic beams, protons, fast neutrons and heavy particles generated by various accelerators to cure cancers, is an important method for treating cancers, and improvement of its efficacy is a research area attracting much study. Generally, the efficacy of radiotherapy can be improved by optimizing dosage distribution of the rays; while a key factor to the optimization of the dosage distribution of rays lies in obtaining precise physiological information on a tumor and surrounding tissues.

It is often proposed, prior to surgery or radiotherapy, to perform positioning and navigation to obtain the physiological information of the tumor and the surrounding tissues, so as to improve the efficacy of radiotherapy. In the state of art, the positioning and navigation involves initial positioning of cancer cell regions of a diseased organ by means of a medical imaging device. Afterwards, the diseased organ is removed by surgical operation or radiotherapy. However, there exists the following problems with the present clinical radiotherapy navigation system.

Firstly, currently the positioning and navigation are mostly based on anatomic images obtained by CT or the like, which cannot precisely identify hypoxic tissues and necrotic lesion. The efficacy of radioactive rays on the tumor is mainly manifested by the killing of active cancer cells, especially the oxygen-enriched cells. Rays act on the cells and cause ionization of water molecule, forming free radicals R., such as OH. free radicals. If there are oxygen molecules in the cells, then the free radicals R. will conduct the following reaction: $R.+O_2 \rightarrow RO_2.$, which will further produce products that is destructive to the molecules in the cells. The prerequisite of the above reaction is the presence of oxygen. Where the tumor tissue is in the hypoxic state, the efficacy of the rays on the tumor will be significantly degraded. Moreover, no radiation is needed to be emitted on the necrotic tissues. Therefore, radiation dosage for the hypoxic tissues and necrotic needs to be adjusted to minimize damage to the healthy tissues of a patient. Therefore, precise identification of the hypoxic tissues and necrotic lesion is of much importance.

Secondly, the treatment of subclinical focus is to a certain extent aimless. Devices such as CT cannot efficiently position the subclinical focus, not to mention providing navigation for radiotherapy. A subclinical focus such as breast cancer is secondary symptoms that appears during the process of cancer incidence, and is typically adjacent to or at places spaced from the tumor. Sometimes there are multiple lesions, which appear to be negative and usually difficult to be identified under the microscope, let alone using regular clinical examination. Patients will very likely face failed treatment if their subclinical focuses were not eliminated.

Thirdly, the positioning and navigation in the state of art cannot report to a doctor or medical physician the information of the tumor and surrounding tissues in real-time. During the radiotherapy, the free radicals will damage the living cells. For example, reduction in activity of tumorous tissues will cause reduction in partial pressure of oxygen, which will in turn lower the ray sensitivity of the lesions. As another example, due to the complexity of the physiological mechanism of human body, various accidental and unpredictable conditions may occur clinically, making it impossible to identify whether the rays will cause irrecoverable damages to the healthy tissues. Therefore, if it is possible to report the physiological feedback of the tumor and surrounding tissues in real-time, the dosage distribution could be adjusted before the rays might otherwise have caused irrecoverable damages to the healthy tissues, which will reduce the harm to the patients, improving the living quality and survival rate of the patients.

Lastly, the dosage distribution obtained with the state of art is not precise enough. When planning the radiotherapy, the influence on the target volume of the repetition errors caused by the breath and organ movements as well as patient position should be taken into consideration, and therefore, to ensure the efficacy of the radiotherapy, the planned target region in the radiotherapy is generally larger than the actual target region by several centimeters. As a result, damages to the healthy tissues will be increased during the radiotherapy, especially when the target region overlaps with the ray-sensitive tissues. Then, there will be a dilemma in that if the target region or dosage is reduced to protect the healthy tissues which are sensitive to the rays, the lesions may not be affected effectively, while if a larger target region and a greater dosage are used to realize a better treatment, the tissues will experience extra radiation dosage, which will cause more serious damage to the tissues. Therefore, if the precision of the dosage distribution may be increased, the damages to the healthy tissues may be reduced.

In summary, from the perspective of radiobiology, improvement on the efficacy of the radiotherapy requires for accurate illustration of the state and change of tissues in terms of physiological information by the radiotherapy navigation and observation device, prompt provision of related information to realize real-time navigation and feedback, and precise dosage distribution on the target region with high resolution.

As a functional imaging technology, positron emission tomography (PET), in comparison with CT, has outstanding advantage in obtaining physiological information of the tumor and surrounding tissues during radiotherapy positioning and navigation. In the meantime, in comparison with MRI, it will not affect the surgical operation due to magnetization of the surgical device. Therefore, it is scientific and efficient to choose the PET imaging technology for radiotherapy navigation during tumor surgery.

Traditional PET employs a plurality of detector components to form an enclosed imaging system of an approximal circular structure. For example, Taiga Yamaya of Japan proposed an Open PET (see An Initial Investigation of Open PET Geometries, 2007 IEEE Nuclear Science Symposium Conference Record), which has a circular detecting ring structure as illustrated in FIG. 1, featuring in using two detection rings 1 and 2 parallel with and spaced from each other, such that radiotherapeutic rays can radiate the human body 3 through the space between the two detection rings. The method solves the problem that the detection rings block the radiotherapeutic rays. Since the sensitivity is proportional to the coverage angle of the detection rings, however, the coverage angle of Open PET decreases with the increase of the distance in the case of using the same number of detectors. In comparison with the traditional PET, the Open PET's sensitivity will be further degraded, which will deteriorate the imaging performance, making it impossible to perform real-time dynamic imaging during the radiotherapy navigation. In order to allow the field of view to cover most of a human torso, moreover, the clinical PET of circular structure typically has an internal diameter greater than 70 cm, sometimes even up to 2 meters, which make the instrument bulky and of complicated structure, such that the medical physician has little operation space, and thus it is still difficult for the PET to be integrated with radiotherapy devices.

SUMMARY

In the disclosure, an objective is to provide a flat-plate PET imagining device with a window, thereby solving the problems of unable to realize real-time positioning and scanning and not having enough operation space during radiotherapy navigation.

In the disclosure, provided is a flat-plate PET imagining device with a window, which comprises: a first flat plate comprising a plurality of PET detectors that are arranged sequentially in a plate shape, and at least one window; a second flat plate comprising a plurality of PET detectors that are arranged in sequentially in a plate shape, the second flat plate being parallel to the first flat plate; and a support device to which the first flat plate and the second flat plate are fixed.

The window has an area that is of integral multiple of an area of the PET detector.

The area of the window is in a range of 1 square centimeter to 1 square meter.

In an embodiment of the invention, the second flat plate comprises at least one window.

In an embodiment of the invention, the first flat plate has a shape identical with that of the second flat plate.

In an embodiment of the invention, the first flat plate has a shape different from that of the second flat plate.

In an embodiment of the invention, the support device comprises: a rotational stand; two first guiding rails arranged in parallel to each other on the rotational stand, and at least two second guiding rails arranged perpendicularly to the first guiding rails and fixed to the first guiding rails by means of first sliding blocks, wherein the first flat plate and the second flat plate are hinged to the second guiding rails by means of second sliding blocks.

The first sliding blocks each comprise a fixing plate arranged perpendicularly to the said first guiding rail and extending towards the other first guiding rail, wherein the second guiding rails are fixed to the fixing plates.

In an embodiment of the disclosure, the support device further comprises a driving motor and a third guiding rail, wherein the rotational stand has a shape of circular, the driving motor comprises a driving gear that engages with the rotational stand, the third guiding rail is arranged perpendicularly to the first guiding rails and the second guiding rails respectively, and the first flat plate and the second flat plate are fixed to the third guiding rail by means of third sliding blocks.

In an embodiment of the disclosure, the PET detector has a shape of triangle or parallelogram.

In the disclosure, provided is a flat-plate PET imagining device with a window, which facilitates real-time diagnosis and positioning of cancerous cells during surgical operation or radiotherapy. It thus can illustrate distribution and physiological information of the cancerous cells in real-time, avoiding positioning errors caused by spreading or change of the cancerous cells. In the meantime, a window is arranged on the flat-plate PET, which helps to provide space for other operations such as radiotherapy while ensuring real-time positioning and scanning effects, thereby achieving real-time diagnosis as well as positioning and navigation without affecting the therapeutic procedure. Moreover, in the disclosure it has proposed to precisely reflect the state and change of tissues by using the physiological and biochemical information, realizing quick imaging during the radiotherapy navigation, thus providing basis and standard for improving the precision of the ray dosage distribution, thereby improving the therapeutic effect.

DETAILED DESCRIPTION

In the following, the invention will be described further with reference to embodiments. It should be understood that the following embodiments are for illustrative instead of limitative purpose only.

Figure 2:
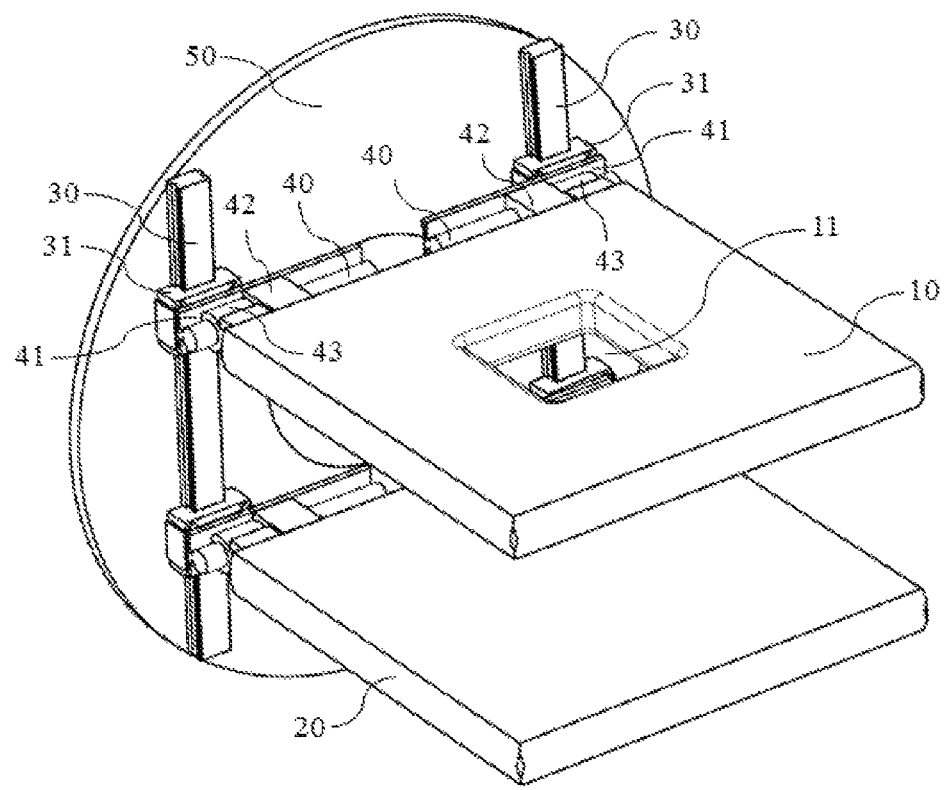
FIG. 2 schematically illustrates a perspective view of a flat-plate PET imaging device with a window in accordance with an embodiment of the invention.

FIG. 2 schematically illustrates a perspective view of a flat-plate PET imaging device with a window in accordance with an embodiment of the invention. In the disclosure, A the flat-plate PET imaging device as shown in FIG. 2 comprises a first flat plate 10, a second flat plate 20 and a support device. The first flat plate 10 and the second flat plate 20 are arranged in parallel and fixed through the support device. Specifically, the support device comprises first guiding rails 30, second guiding rails 40 and a rotational stand 50. The two first guiding rails 30 are arranged in parallel to each other, and disposed on a side of the circular flat-shaped rotational stand 50, each first guiding rail 30 being provided with two first sliding blocks 31, which are snapped onto and slidable along the first guiding rails 30. Each of the first sliding block 31 is further provided with a fixing plate 41 perpendicular to the first guiding rail 30 and extending towards the opposite first guiding rail 30. The second guiding rails 40 are perpendicular to the first guiding rails 30 and fixed to the fixing plate 41 by way of fixing blocks 42. The first flat plate 10 and the second flat plate 20 are respectively hinged to the second guiding rails 40 through second sliding blocks 43, such that the first flat plate 10 and the second flat plate 20 can slide along the second guiding rails 40 while they are respectively rotatable around the second guiding rails 40. Formed in the first flat plate 10 is a window 11, which can facilitate the medical physician to perform other operations, such as introducing X-rays through the window 11, during the radiotherapy navigation.

Figure 3:
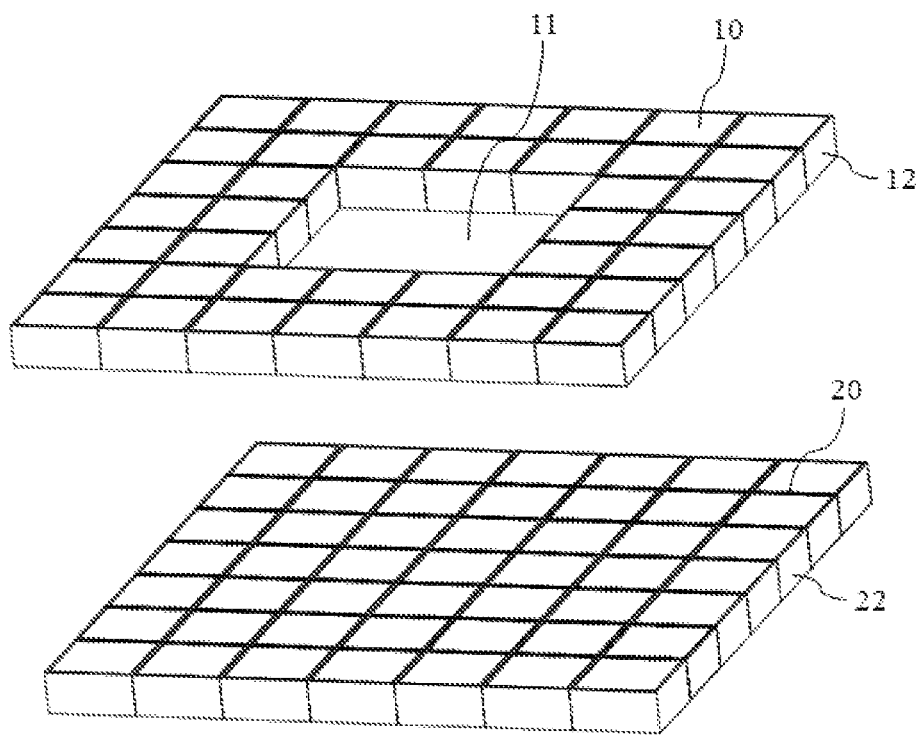
FIG. 3 schematically illustrates an arrangement of detector arrays and window of the flat-plate PET imaging device with the window as shown FIG. 2.

FIG. 3 schematically illustrates an arrangement of detector arrays and window of the first flat plate 10 and the second flat plate 20 as shown in FIG. 2. As shown in FIG. 3, the first flat plate 10 and the second flat plate 20 each comprise a plurality of PET detectors 12, 22 arranged sequentially. The PET detectors 12, 22 may be connected to each other by conventional means, such as by means of mechanical parts or fixture connection. The first flat plate 10 and the second flat plate 20 as needed may have various shapes, such as a circle or a ring. Similarly, the first flat plate 10 and the second flat plate 20 may be adjusted to be of different or same sizes as needed. In FIG. 3, the first flat plate 10 and the second flat plate 20 are each as a rectangular plate with the same size. Herein the first flat plate 10 is formed with the window 11 by removing 3 by 3 PET detectors in the center. The size of the window 11 is approximately equal to nine times the area of one single PET detector 12. Generally, the area of the window 11 is integral multiple(s) of the area of one single PET detector. As the individual PET detectors as needed may have different sizes by cutting, such that the area of one single window may be from 1 square centimeter to 1 square meter.

It is noted that in the disclosure the location, number and size of the window 11 is adjustable as needed. For example, the location of the window may be variously adjusted in any flat plate, the number of the window may be two or more, or the first and second flat plates each may have the respective window. Other embodiments are illustrated in FIGS. 4 to 6, which are for illustrative purpose only, but not as limitation.

Figure 4:
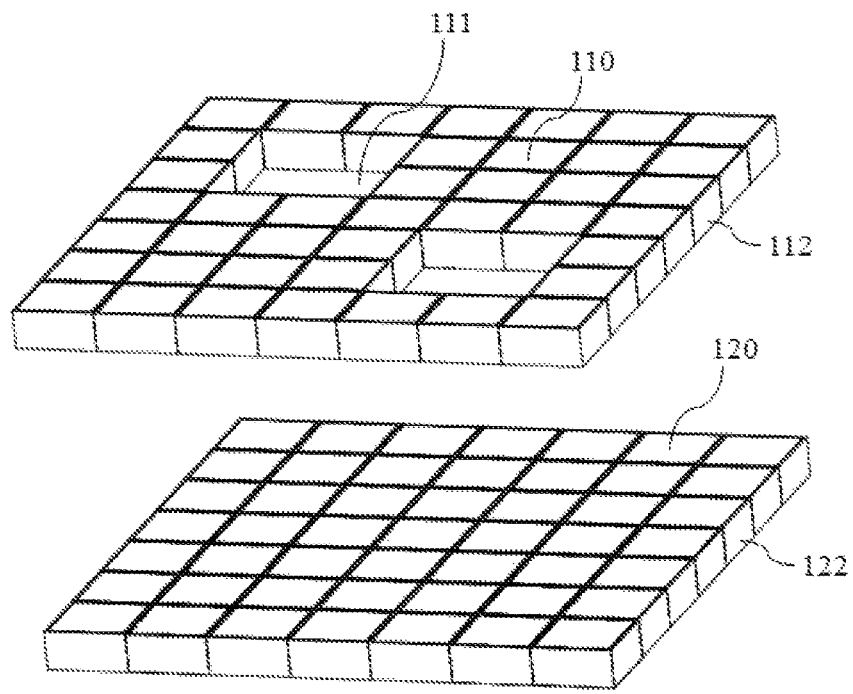
FIG. 4 schematically illustrates an arrangement of detector arrays and window according to another embodiment of the invention.

As illustrated in FIG. 4, in another embodiment of the invention, in which numeral reference for the like element is indicated by numbers increased by 100, formed in the first flat plate 110 are two windows 111, which are approximately arranged in the diagonal line of the first flat plate 110, each window 111 having an area four times that of the single PET detector.

Figure 5:
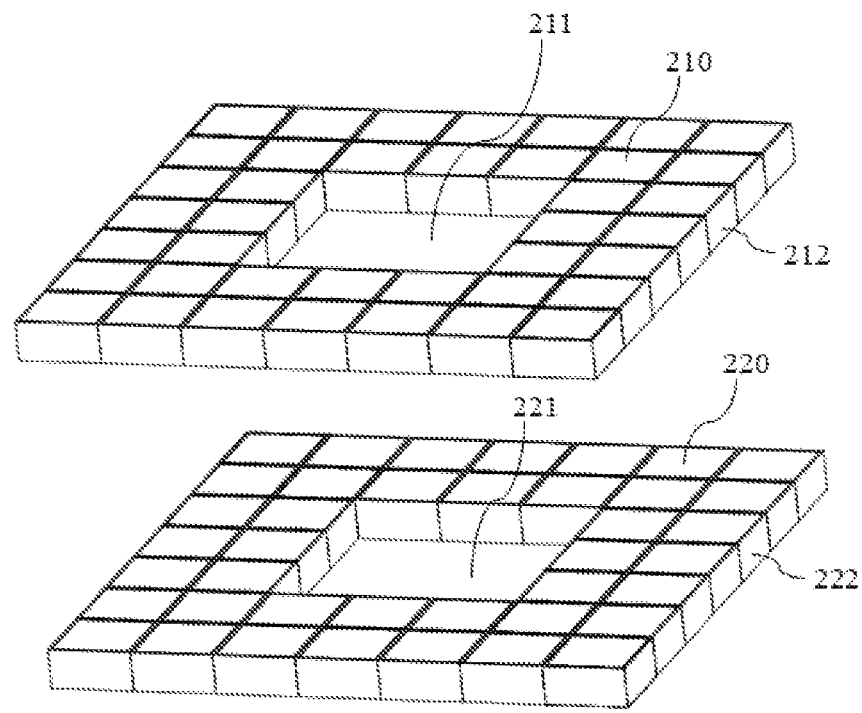
FIG. 5 schematically illustrates an arrangement of detector arrays and windows according to another embodiment of the invention.

As illustrated in FIG. 5, in another embodiment of the invention, in which numeral reference for the like element is indicated by numbers increased by 200, arranged on the first flat plate 210 is a window 211, which has an area nine times that of one single PET detector. Formed centrally in the second flat plate 220 is a window 221, which has a location corresponding to that of window 211. Similarly, the window 221 has an area nine times that of the single PET detector.

Figure 6:
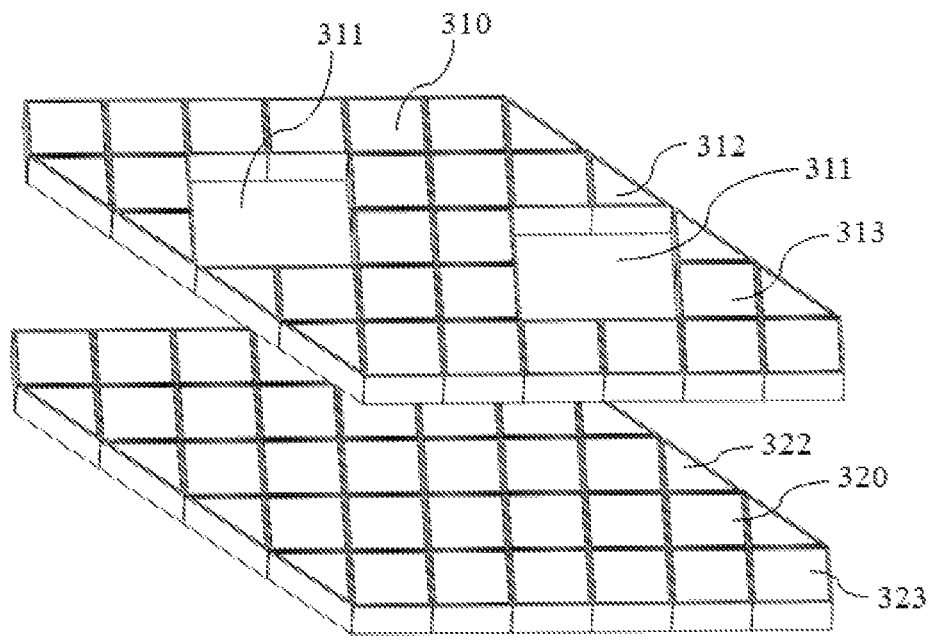
FIG. 6 schematically illustrates an arrangement of detector arrays and windows according to another embodiment of the invention.

Moreover, as illustrated in FIG. 6, in another embodiment of the invention, in which numeral reference for the like element is indicated by numbers increased by 300, the first flat plate 310 and the second flat plate 320 as illustrated each are irregular combined plate, that is, the first flat plate 310 and the second flat plate 320 each are formed by triangular PET detectors 312, 322 and square PET detector 313, 323 arranged sequentially. In the embodiment, formed in the first flat plate 310 are two windows 311, each of which has an area about four times the area of the single PET detector 313.

In the disclosure, it is proposed to use two parallel PET flat plates, which may be used for scanning and imaging in the procedure of treating tumors, so as to thus track and position the tumors cells in real time. In the disclosure, it proposed to form window(s) in the PET plate(s) as needed, such that a spatial channel may be formed in the direction perpendicular to the flat plate(s) in between the two flat plate(s), thereby allowing enough space for the tumor treatment operation for the medical physician or for the rays to pass. Meanwhile, less detectors are required and thus the cost is reduced.

In the disclosure, in use, a distance between the first flat plate 10 and the second flat plate 20 may be adjustable by means of a driving mechanism (not shown) along the first guiding rails 30, as illustrated in FIG. 2, in order to better adapt to the size of the tumor region. Meanwhile, the first flat plate 10 and the second flat plate 20 may be respectively moveable along the second guiding rails 40 in a direction perpendicular to the first guiding rails 30, such that a relative position between the first flat plate 10 and the second flat plate 20 may be adjustable so as to achieve an improved imaging effect. Moreover, the first flat plate 10 and the second flat plate 20 may also be synchronically rotatable around the respective second guiding rail 40 so as to change an inclination direction and a relative position of the window(s). There will be little impact on the overall detection precision by arranging windows in the flat plate PET.

Figure 1:
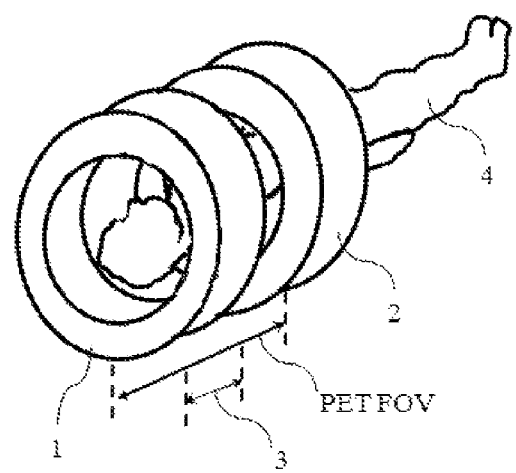
FIG. 1 schematically illustrates a circular detection ring structure of a conventional Open PET.
Figure 7:
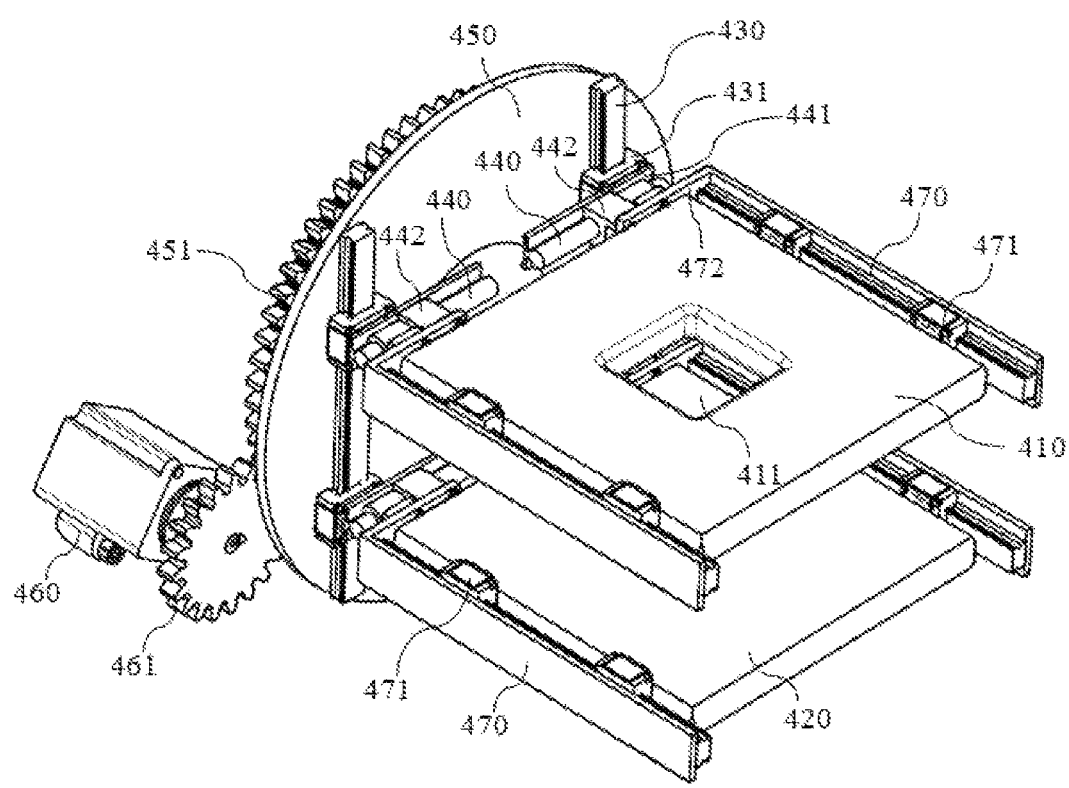
FIG. 7 schematically illustrates a perspective view of a flat-plate PET imaging device with a window according to another embodiment of the invention.

Moreover, illustrated in FIG. 7 is another embodiment of the invention, in which numeral reference for the like element is indicated by numbers increased by 400, in which the first flat plate 410, the second flat plate 420, the first guiding rails 430, the second guiding rails 440 and the rotational stand 450 are all the same as those of the embodiment as shown in FIG. 1. In the following only the different elements will be described. In FIG. 7, the embodiment further comprises a driving motor 460, which comprises a driving shaft on which a driving gear 461 is arranged, and third guiding rails 470. Arranged circumferentially on the rotational stand 450 are engaging teeth 451 which are configured to engage with the driving gear 461 such that the rotational stand 450 is driven to rotate by the driving motor 460, such that the first flat plate 410 and the second flat plate 420 are rotated to the required positions. The fixing blocks 442 are each provided with a third fixing plate 472 which extends perpendicularly to the first guiding rails 430. Arranged on the third fixing plate 472 is a third guiding rail 470 perpendicular to the first guiding rails 430 and the third fixing plate 472. Arranged respectively on two opposite sides of the first flat plate 410 or the second flat plate 420 are two third sliding blocks 471, which are snapped into the third guiding rails 470, such that the first flat plate 410 or the second flat plate 420 may be slidable along the third guiding rails 470. In the embodiment, the first flat plate 410 or the second flat plate 420 may realize three dimensional linear movements, i.e., along the first guiding rails 430, the second guiding rails 440 or the third guiding rails 470. They may also realize a rotational movement around the rotational stand 450. As a result, the first flat plate 410 and the second flat plate 420 may be positioned as desired according to the therapeutic requirement.

In the disclosure, the flat plate PET detection system with a window is able to facilitate positioning and navigation before the surgical operation or radiotherapy, effective identification of tissues such as residual lesions, necrotic lesions, and sub-clinical lesions, thereby improving the treatment success rate. In the disclosure, it may be combined with other imaging device to perform same-bed, same-time, and multi-modal imaging, thereby eliminating the impact caused by the tissue variation within the scanning time difference and eliminating errors in the image merge. It may be used together with devices such as microscope and "Da Vince surgery system" for detecting and finding other physiological and biochemical phenomena in clinical or biological research.

What is described above is preferred embodiments of the invention and shall not be construed as limitation to the scope of the invention. It should be understood that various alternatives to the embodiments of the invention described herein may be employed. It is thus intended that apparent or equivalent changes and variations to the embodiments as recited in the claims and description, which are considered to be within the ability of those skilled in the art, are all to be within the scope of the invention. For example, in FIG. 2 the window 11 may be configured to extend in a direction perpendicular to the first guiding rails 30 so as to divide the first flat plate 10 into two separate flat plates. As another example, in FIG. 5 the window 211, 221 may be configured respectively to extend in a direction perpendicular to the first guiding rails so as to divide each of the first flat plate 210 and the second flat plate 220 into two separate flat plates. As still another example, the support device in the disclosure may be configured as other form that is able to be universally moveable, which will not be elaborated here. There are conventional configurations that are not detailedly described herein and to be covered by the invention.

What is claimed is:

1. A flat-plate PET imaging device with a window, wherein the flat-plate PET imaging device comprises:
    a first flat plate comprising a first array of PET detectors that are arranged sequentially in a plate shape side by side and at least one first window;
    a second flat plate comprising a second array of PET detectors that are arranged sequentially in a plate shape side by side, the second flat plate being parallel to the first flat plate; and
    a support device to which the first flat plate and the second flat plate are fixed,
    wherein the at least one first window has an area that is of integral multiple of an area of one of the first array of PET detectors by omitting or removing at least one of the first array of PET detectors.

2. The flat-plate PET imaging device with the window of claim 1, wherein the window has an area that is of integral multiple of an area of the PET detector.

3. The flat-plate PET imaging device with the window of claim 2, wherein the area of the window is in a range of 1 square centimeter to 1 square meter.

4. The flat-plate PET imaging device with the window of claim 1, wherein the second flat plate comprises at least one second window.

5. The flat-plate PET imaging device with the window of claim 1, wherein the first flat plate has a shape identical with that of the second flat plate.

6. The flat-plate PET imaging device with the window of claim 1, wherein the first flat plate has a shape different from that of the second flat plate.

7. The flat-plate PET imaging device with the window of claim 1, wherein the support device comprises:
    a rotational stand;
    two first guiding rails arranged in parallel to each other on the rotational stand; and
    at least two second guiding rails arranged perpendicularly to the first guiding rails and fixed to the first guiding rails by means of first sliding blocks, wherein the first flat plate and the second flat plate are hinged to the second guiding rails by means of second sliding blocks.

8. The flat-plate PET imaging device with the window of claim 7, wherein the first sliding blocks each comprise a fixing plate arranged perpendicularly to the first guiding rail and extending towards the other first guiding rail, wherein the second guiding rails are fixed to the fixing plates.

9. The flat-plate PET imaging device with the window of claim 7, wherein the support device further comprises a driving motor and a third guiding rail, wherein the rotational stand has a shape of circular, the driving motor comprises a driving gear that engages with the rotational stand, the third guiding rail is arranged perpendicularly to the first guiding rails and the second guiding rails respectively, and the first flat plate and the second flat plate are fixed to the third guiding rail by means of third sliding blocks.

10. The flat-plate PET imaging device with the window of claim 9, wherein the PET detector has a shape of triangle or parallelogram.

11. The flat-plate PET imaging device with the window of claim 4, wherein the second window has an area that is of integral multiple of an area of one of the second array of PET detectors by omitting or removing at least one of the second array of PET detectors.

12. A flat-plate PET imaging device with a window, wherein the flat-plate PET imaging device comprises:
    a first flat plate comprising a plurality of PET detectors that are arranged sequentially in a plate shape, and at least one window;
    a second flat plate comprising a plurality of PET detectors that are arranged sequentially in a plate shape, the second flat plate being parallel to the first flat plate; and
    a support device to which the first flat plate and the second flat plate are fixed, wherein the support device comprises:
    a rotational stand;
    two first guiding rails arranged in parallel to each other on the rotational stand; and
    at least two second guiding rails arranged perpendicularly to the first guiding rails and fixed to the first guiding rails by means of first sliding blocks, wherein the first flat plate and the second flat plate are hinged to the second guiding rails by means of second sliding blocks.

13. The flat-plate PET imaging device with the window of claim 12, wherein the first sliding blocks each comprise a fixing plate arranged perpendicularly to the first guiding rail and extending towards the other first guiding rail, wherein the second guiding rails are fixed to the fixing plates.

14. The flat-plate PET imaging device with the window of claim 12, wherein the support device further comprises a driving motor and a third guiding rail, wherein the rotational stand has a shape of circular, the driving motor comprises a driving gear that engages with the rotational stand, the third guiding rail is arranged perpendicularly to the first guiding rails and the second guiding rails respectively, and the first flat plate and the second flat plate are fixed to the third guiding rail by means of third sliding blocks.

15. The flat-plate PET imaging device with the window of claim 14, wherein the PET detector has a shape of triangle or parallelogram.

16. The flat-plate PET imaging device with the window of claim 12, wherein the window has an area that is of integral multiple of an area of the PET detector.

17. The flat-plate PET imaging device with the window of claim 16, wherein the area of the window is in a range of 1 square centimeter to 1 square meter.

18. The flat-plate PET imaging device with the window of claim 12, wherein the second flat plate comprises at least one window.

19. The flat-plate PET imaging device with the window of claim 12, wherein the first flat plate has a shape identical with that the second flat plate.

20. The flat-plate PET imaging device with the window of claim 12, wherein the first flat plate has a shape different from that of the second flat plate.

* * * * *